United States Patent
Lang et al.

(10) Patent No.: US 9,004,062 B2
(45) Date of Patent: Apr. 14, 2015

(54) DEVICE FOR DOSED ADMINISTRATION OF SPRAYABLE SUBSTANCES WITH OPERATING AND RELEASE OPTIONS

(75) Inventors: Sven Markus Lang, Bad Schoenborn (DE); Kai Tiesberger, Niedernhausen (DE)

(73) Assignee: Sanner GmbH, Bensheim (DE)

( * ) Notice: Subject to any disclaimer, the term of this patent is extended or adjusted under 35 U.S.C. 154(b) by 1031 days.

(21) Appl. No.: 12/319,656

(22) Filed: Jan. 8, 2009

(65) Prior Publication Data

US 2009/0151723 A1    Jun. 18, 2009

(51) Int. Cl.
*A61M 11/00* (2006.01)
*A61M 15/00* (2006.01)

(52) U.S. Cl.
CPC ....... *A61M 15/009* (2013.01); *A61M 2205/581* (2013.01); *A61M 15/008* (2014.02)

(58) Field of Classification Search
USPC ............. 128/200.14–200.23, 202.27, 204.21, 128/205.23; 222/23–48, 153.01–153.14, 222/402.1, 402.11
See application file for complete search history.

(56) References Cited

U.S. PATENT DOCUMENTS

| | | | |
|---|---|---|---|
| 3,006,340 A * | 10/1961 | Meshberg | 128/200.23 |
| 3,306,252 A * | 2/1967 | Knight et al. | 128/200.23 |
| 3,422,996 A * | 1/1969 | Lipman | 222/402.11 |
| 3,610,480 A * | 10/1971 | Lipfert et al. | 222/402.11 |
| 4,159,067 A * | 6/1979 | Akers | 222/153.02 |
| 4,830,224 A * | 5/1989 | Brison | 222/153.06 |
| 5,335,823 A * | 8/1994 | Fuchs et al. | 222/36 |
| 5,411,173 A | 5/1995 | Weinstein | 222/38 |
| 5,575,280 A | 11/1996 | Gupte et al. | 128/203.15 |
| 5,611,444 A * | 3/1997 | Garby et al. | 215/230 |
| 5,743,252 A | 4/1998 | Rubsamen et al. | 128/200.14 |
| 6,109,479 A * | 8/2000 | Ruckdeschel | 222/82 |
| 6,113,008 A * | 9/2000 | Arsenault et al. | 239/337 |

(Continued)

FOREIGN PATENT DOCUMENTS

EP   0 028 929   5/1981
EP   0 448 204   4/1995

(Continued)

OTHER PUBLICATIONS

Office Action dated Dec. 20, 2011 in Japanese Patent Application No. 2009-518,771.

*Primary Examiner* — Rachel Young
(74) *Attorney, Agent, or Firm* — Greer, Burns & Crain, Ltd.

(57) ABSTRACT

A device for dosed administration of a sprayable substance, in particular aerosols, with an electronic unit for recording the administrations. The device includes a first housing part that forms a seat for a container, which contains the sprayable substance and has a valve. The device also includes a second housing part, which is movable relative to the first housing part and has an actuating part for acting on the valve to actuate the valve for administration of the sprayable substance. The electronic unit records the administrations of the sprayable substance and includes a switch that is actuated by the relative movement of first and second housing parts.

20 Claims, 8 Drawing Sheets

Section III - III

(56) References Cited

U.S. PATENT DOCUMENTS

| | | | |
|---|---|---|---|
| 6,138,669 A | 10/2000 | Rocci, Jr. et al. | 128/200.23 |
| 6,202,642 B1* | 3/2001 | McKinnon et al. | 128/200.23 |
| 6,578,573 B2* | 6/2003 | Koch | 128/202.27 |
| 6,651,844 B2* | 11/2003 | Tomaka et al. | 222/38 |
| 6,918,512 B2* | 7/2005 | Kondoh | 222/153.09 |
| 2003/0000524 A1* | 1/2003 | Anderson et al. | 128/203.23 |
| 2003/0133877 A1* | 7/2003 | Levin | 424/45 |
| 2005/0098172 A1* | 5/2005 | Anderson | 128/200.23 |
| 2005/0252508 A1* | 11/2005 | Koerner et al. | 128/200.14 |

FOREIGN PATENT DOCUMENTS

| | | |
|---|---|---|
| EP | 0 684 047 | 11/1995 |
| EP | 0 775 499 | 5/2003 |
| WO | WO 02/24269 | 3/2002 |
| WO | WO 02/36190 | 5/2002 |
| WO | WO 2005/079997 | 9/2005 |
| WO | WO 2006/004498 | 1/2006 |

* cited by examiner

Section III - III

Section L-L

Section XII-XII

Section XIII-XIII

DEVICE FOR DOSED ADMINISTRATION OF SPRAYABLE SUBSTANCES WITH OPERATING AND RELEASE OPTIONS

PRIORITY CLAIM

This application is a §371 application of and claims priority to PCT Application No. PCT/EP2007/006052 filed on Jul. 9, 2007, which claims priority to and the benefit of German Patent Application No. DE 10 2006 032 293.3 filed on Jul. 11, 2006, both of which are hereby incorporated by reference in their entireties.

FIELD OF THE INVENTION

The present invention relates to a device for the dosed administration of sprayable substances, especially aerosols, including an electronic unit to record the administered doses, and including a first housing part that forms a receptacle for a canister having a valve and containing the sprayable substance.

BACKGROUND OF THE INVENTION

Such devices for the dosed administration of sprayable substances can especially be configured as inhalers and can be employed in medicine for the treatment of diseases. Such inhalers are suitable, for instance, to treat asthma, allergies or other diseases and, in particular, they serve for the dosed administration of a drug that is delivered via the mouth or nose. In this context, one also speaks of so-called metered-dose aerosols. Especially when it comes to life-threatening diseases, it is important for the user to have information about how much of the substance is still left in the canister. As a rule, this is not visible since the pressurized canister that holds the sprayable substance is usually not made of a transparent material. This underscores the importance of an electronic unit to record the administered doses of the sprayable substance. This unit provides users with reliable information about the amount of sprayable substance that has been administered or that is still left in the canister, so that they can make sure that they always have an adequate supply of the sprayable substance they need.

Devices for the dosed administration of drugs are known in various configurations. For instance, European patent application EP 0 448 204 B1 discloses such a device having a one-piece housing with a receptacle for a canister that holds the sprayable substance. The housing has a hollow mouthpiece that is arranged at an angle relative to the longitudinal axis of the canister and through which the sprayable substance can be delivered and inhaled when a valve on the canister is actuated. The sprayable substance is administered in that the canister moves towards the housing and, in this process, the valve on the canister is actuated. In order to record the number of administered doses, the prior-art device is provided with an electronic unit that has a switch that is situated directly on the canister and that is actuated by it.

Another inhaler is described in European patent application EP 0 775 499 B1. Here, a unit that is supposed to show the number of administered doses is arranged on the upper end of the housing.

In the case of the inhaler described in U.S. Pat. No. 6,138,669, the number of administered doses is recorded by a sensor that measures the pressure pulse in the transfer channel of the mouthpiece.

SUMMARY OF THE INVENTION

Before this background, the invention sets itself an objective of putting forward a device that is easy to operate and that reliably records the number and/or the duration of the administered doses of the sprayable substance.

The present invention provides a generic device for the dosed administration of sprayable substances in that it has a second housing part that can be moved relative to the first housing part and an actuating section that acts upon the valve to cause the valve to deliver the sprayable substance, whereby the electronic unit to record the administered doses of the sprayable substance has a switch that is actuated by the relative movement of the first and second housing parts.

The device according to the invention is advantageous. Thus, the delivery of the sprayable substance is recorded independently of the canister, since the switch is actuated by the relative movement of the first and second housing parts. For this reason, the device can even function irrespective of the precise shape and/or size of the canister being used, so that one and the same device can be used in conjunction with different canisters. Here, the delivery of the sprayable medium can be reliably recorded every time.

The sprayable substance is preferably present in the form of a liquid or a powder. The sprayable substance can also comprise a solution and/or a mixture of various substances. In particular, the sprayable substance can be a therapeutically effective composition such as a drug.

An improvement is achieved in that the first and second housing parts are joined, especially by means of a bayonet lock, in such a way that the first and second housing parts can assume an operating position and a release position with respect to each other, whereby, in the operating position, the first and second housing parts can move in the axial direction with respect to each other and whereby, in the release position, the second housing part can be removed from the first housing part. Therefore, in the operating position, the two housing parts can be moved towards each other in order to actuate the valve of the canister. In the release position, the second housing part can be removed, for example, in order to be cleaned.

Inadvertent actuations during assembly, for example, after cleaning the device, can be prevented since, when the first and second housing parts are in the release position, they cannot be moved axially with respect to each other in such a way that the valve could be actuated by the second housing part.

According to an advantageous embodiment of the invention, it is provided that the switch is a mechanical switch, a proximity switch, an electromagnetic switch and/or an optical switch. In this manner, an electric signal is generated that makes it possible to record the administration of the sprayable medium. A mechanical switch that opens and closes an electric contact can be produced particularly cost-effectively and is especially suitable for disposable products.

Another improvement is achieved in that the switch is configured so that it is not situated on the canister. Then, the switch can be actuated completely independently of the canister, especially independently of its size or shape.

According to the present invention, it can also be provided that the canister, which has a canister body and a canister head with the valve for the dosed administration of the sprayable substance, can be accommodated, at least partially, in the receptacle. In this context, the first housing part can have a hollow shaft in which the canister body can be partially or completely accommodated.

The inhalation of a sprayed substance is facilitated in that the second housing part has a first section to accommodate the canister head and a hollow second section that runs especially at an angle relative to the first section. Here, it has proven advantageous for the hollow second section to be configured as a mouthpiece and/or nosepiece.

In particular, it is easier to clean the device if the second housing part can be removed. Then, after this housing part has been removed, it can be cleaned separately, for example, under running water.

Advantageously, the electronic unit to detect the administered doses records the number and/or the duration of the administered doses. If the canister is one with a metering valve that releases a uniform amount of the substance every time it is actuated, the number of actuations can already indicate the amount that is left in the canister.

If the electronic unit to record the administered doses has an electronic computing unit and an electronic data storage unit, than the administered doses recorded by the switch can be counted in a particularly simple manner. As a result, the unit can easily determine the remaining amount, provided that information about the maximum number of administered doses had been previously stored.

According to a particularly advantageous embodiment of the invention, it is provided that the electronic unit to record the administered doses has a visual display that can show information about the number of administered doses and/or the number of doses remaining. Examples of displays are inexpensive LCDs or some other type of display.

A further improvement is achieved in that the electronic unit to record the administered doses has an acoustic signal transmitter. In this case, the user can be informed, for example, about erroneous operation. It is likewise conceivable to employ such a signal transmitter in order to remind the user that it is time for the next inhalation of the substance.

Advantageously, the electronic unit having the switch to record the administered doses is arranged on or in the first or second housing part and the switch is actuated by an actuation element provided on the other housing part when the first and second housing parts move with respect to each other. Preferably, the electronic unit is arranged on or in the first housing part since then the second housing part is easy to clean without interfering with the electronic unit.

According to the invention, it can also be provided that the device is configured as an inhaler, especially for a drug.

In the finished product, it can be provided that a canister filled at least partially with the sprayable substance is accommodated in the receptacle. In this context, the sprayable substance preferably can be a drug or another therapeutically effective composition.

The administration of the sprayable substance is particularly simple if the substance is kept under excess pressure in the canister.

Dosing is simple and precise if the valve of the canister is configured as a metering valve that delivers a uniform amount—especially in the form of a pulse—of the sprayable substance every time it is actuated.

Additional objectives, features, advantages and application possibilities of the present invention ensue from the description below of an embodiment making reference to the drawings. In this context, all of the features described and/or depicted, either on their own or in any combination, constitute the subject matter of the invention, also independently of their being combined in the individual claims or of their reference back to other claims.

BRIEF DESCRIPTION OF THE DRAWINGS

The following is shown.

DETAILED DESCRIPTION

The figures show a device for the dosed administration of sprayable substances, which is configured as an inhaler. This inhaler serves to administer liquid or solid substances, especially as aerosols, via the respiratory tract. Sprayable substances, especially drugs or other therapeutically effective substances, can be delivered by means of the device.

The device shown in the figures has a first housing part 1 and a second housing part 2. A canister 3 that holds the sprayable substance is accommodated in the first and second housing parts 1, 2.

It can be seen especially in FIGS. 3 to 6a that the canister 3 has a canister head 6 fitted with a valve 5 (not shown here in greater detail) and a canister body 7. Here, the canister 3 is configured as a pressurized canister made of metal that holds the sprayable substance under excess pressure. Due to this excess pressure, the sprayable substance can be automatically delivered when the valve 5 is actuated.

The valve 5 is configured as a metering valve that delivers a constant amount, especially in the form of a pulse—of the sprayable substance—when it is actuated. In this manner, the user can dose the sprayable substance simply by actuating the valve 5 one or more times. The valve 5 has a protruding hollow valve pin 11 by means of which the valve 5 can be actuated. In this process, the valve 5 is held in the closed position by a spring (not shown here) and can be moved into the open position when pressure is exerted on the movable valve pin 11.

Figure 3:
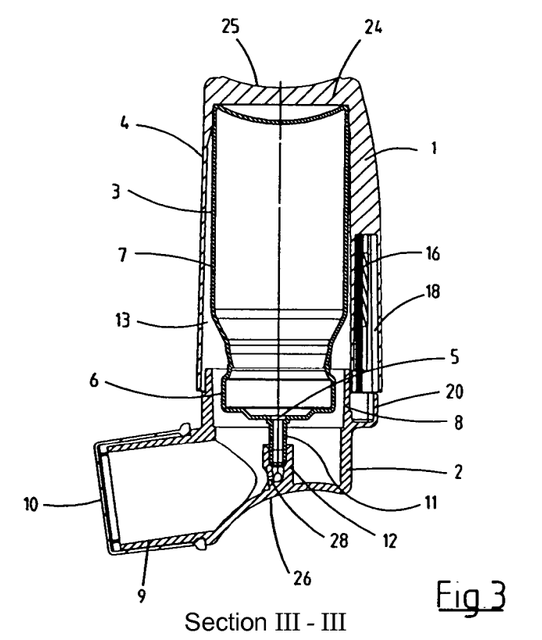
FIG. 3: a section through the device from FIG. 2, along the line A-A.

The first housing part 1 forms a receptacle 13 for the canister body 7 and, for this purpose, has an elongated hollow shaft 4. FIG. 3 shows that the entire canister body 7 is accommodated in the cylindrical receptacle 13. Here, the canister body 7 lies against the first housing part 1. One end of the first housing part 1 has a bottom section 24 whose outside forms a first gripping section 25. The housing part 1 is open on the opposite end.

Figure 4:
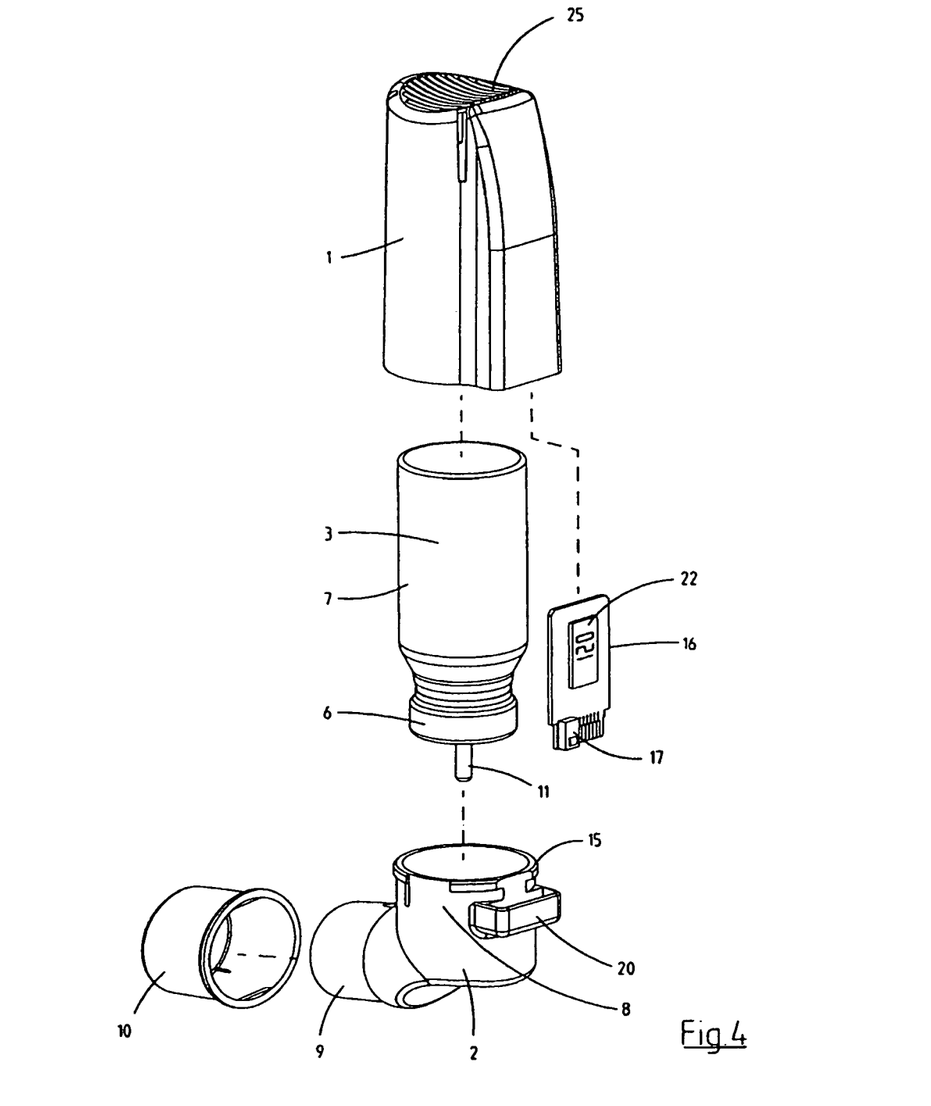
FIG. 4: an exploded view of the device from FIG. 1.

The second housing part 2 has a first section 8 to accommodate the canister head 6 and it can be moved relative to the first housing part 1 in the lengthwise direction of the valve pin 11. An actuating section 12 for the valve 5 is formed in the first section 8. The actuating section 12 lies against the valve pin 11 and accommodates the free end of the valve pin 11. A second section 9 of the second housing part 2 is configured so as to be hollow and oriented at an angle relative to the first section 8. In the embodiment shown, the hollow second section 9 forms a mouthpiece. As an alternative, the second section 9 can also be configured, for example, as a nosepiece if the sprayable substance is meant to be administered into the nose. When not in use, the hollow second section 9 is protected by a removable cap 10, as can be seen in FIGS. 3 and 4. The second housing part 2 also has a second curved gripping section 26 that is located opposite from the first gripping section 25 of the first housing part 1.

When pressure is exerted on both opposite gripping sections 25, 26, the second housing part 2 is moved towards the first housing part 1 and in this process, the valve pin 11 is pushed by the actuating section 12, as a result of which the valve 5 is opened. A dose of the sprayable substance exits via the hollow valve pin 11 and is deflected by a hole 28 formed in the actuating section 12 in such a way that the sprayable substance can exit from the hollow section 9. Subsequently, the pressure on the gripping sections 25, 26 can be reduced or eliminated, after which the first and second housing parts 1, 2 return to their initial position under the action of the spring of the valve 5. In order to facilitate the return to the initial position, it is also possible to provide a spring element (not shown here) directly between the first and second housing parts 1, 2.

Figure 1:
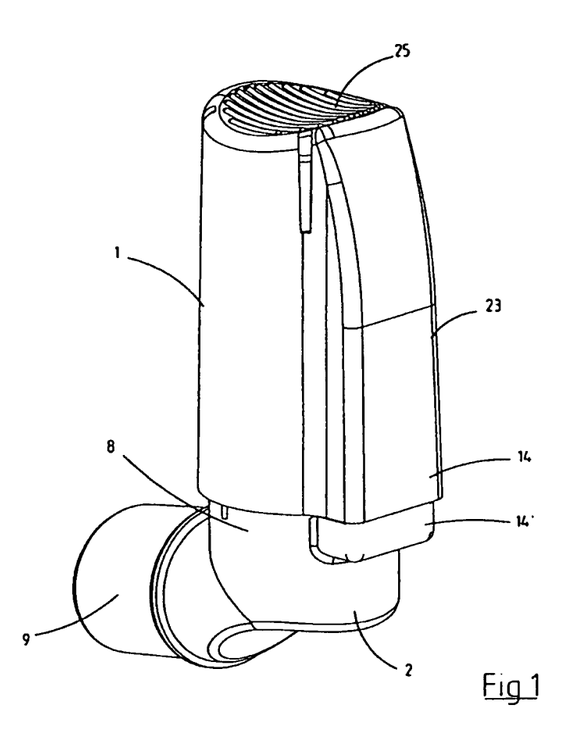
FIG. 1: a perspective view of a device according to the invention for the dosed administration of sprayable substances.
Figure 2:
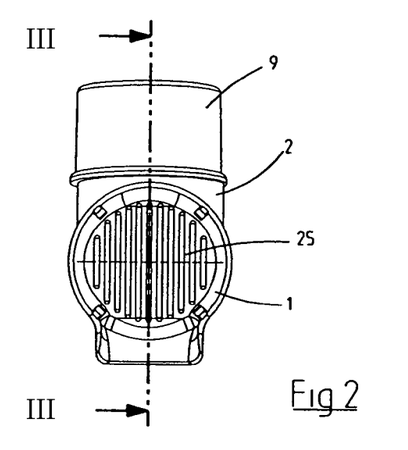
FIG. 2: a top view of the device from FIG. 1.
Figure 10:
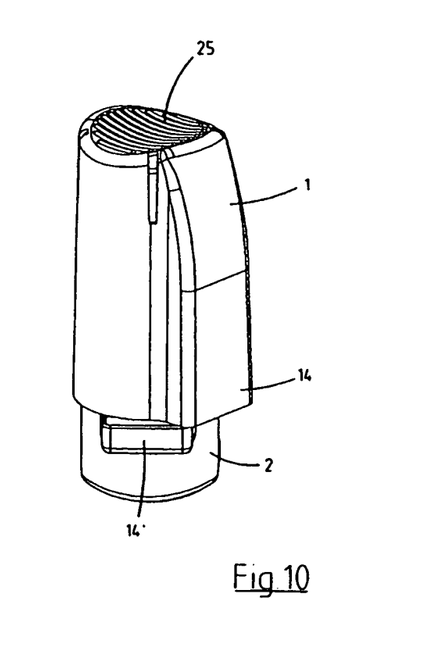
FIG. 10: the device from FIG. 1, whereby the first and second housing parts are rotated with respect to each other.
Figure 11:
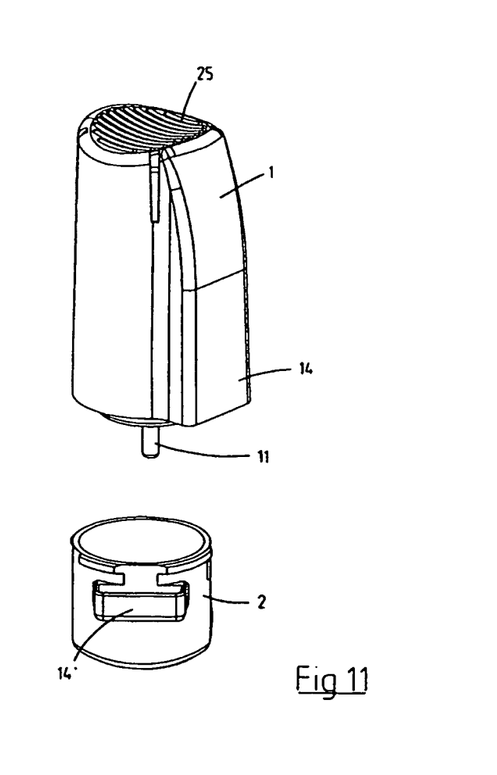
FIG. 11: the device from FIG. 10, whereby the second housing part has been removed.
Figure 12:
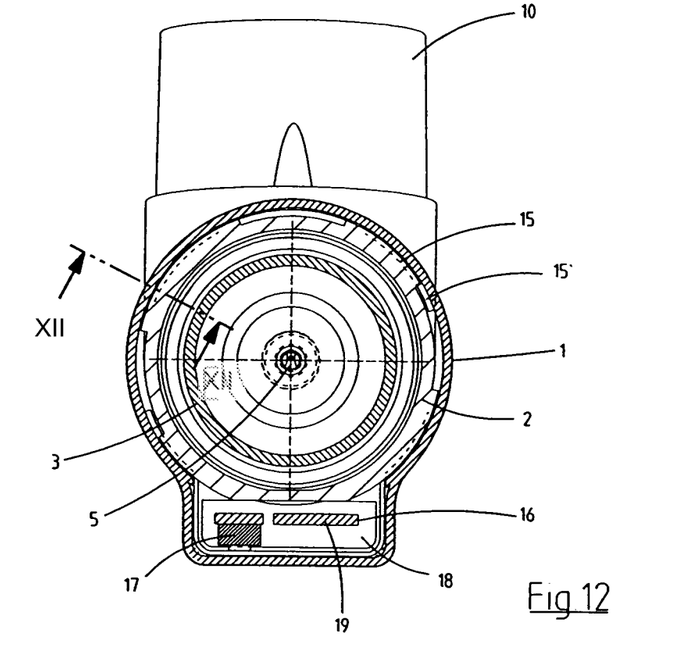
FIG. 12: a section through the device from FIG. 1 in the operating position.
Figure 13:
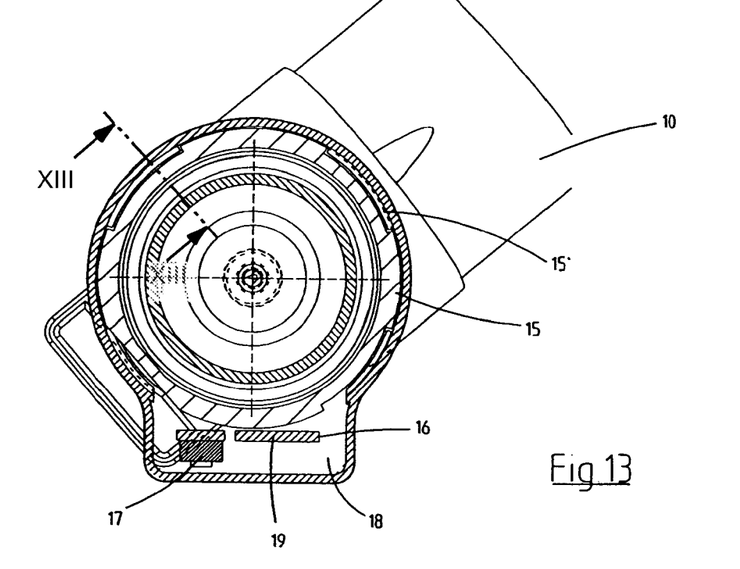
FIG. 13: a section through the device from FIG. 10 in the release position.

The second housing part 2 can be removed from the first housing part 1 so as to facilitate cleaning. Whereas FIGS. 1, 3 and 12 show the first and second housing parts 1, 2 in their operating position, the release position is shown in FIGS. 10 and 13. The first and second housing parts 1, 2 can be rotated with respect to each other, thus moving from the operating position into the release position. For this purpose, the first and second housing parts 1, 2 are joined by means of a bayonet lock that allows the second housing part 2 to be removed from the first housing part 1 in the release position. This can be seen particularly clearly in FIGS. 10 to 13, whereby FIG. 12 shows the operating position while FIGS. 10 and 13 show the release position. Only in the operating position can the first and second housing parts 1, 2 be moved in the axial direction with respect to each other, thus actuating the valve 5. This is not possible in the release position since the housing parts have stops 14, 14' that only allow an axial movement towards each other in when in the operating position. This prevents unintentional actuations during the assembly.

Figure 12A:
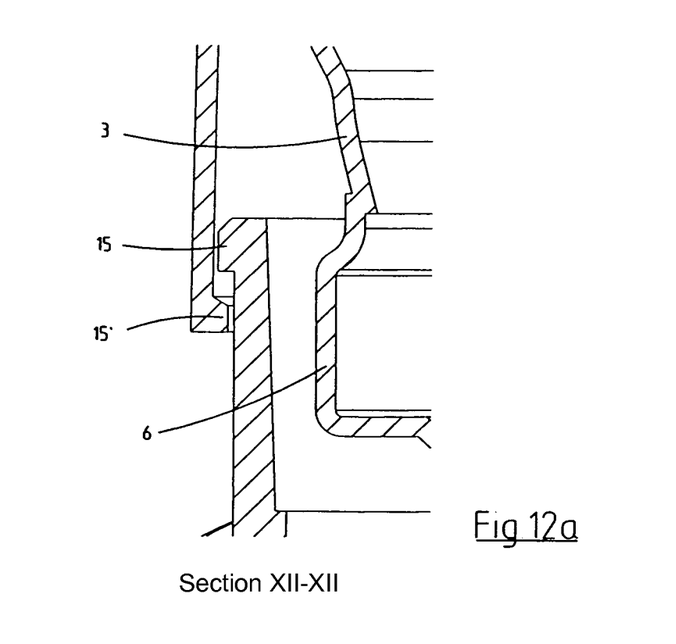
FIG. 12a: a section along the line E-E from FIG. 12.
Figure 13A:
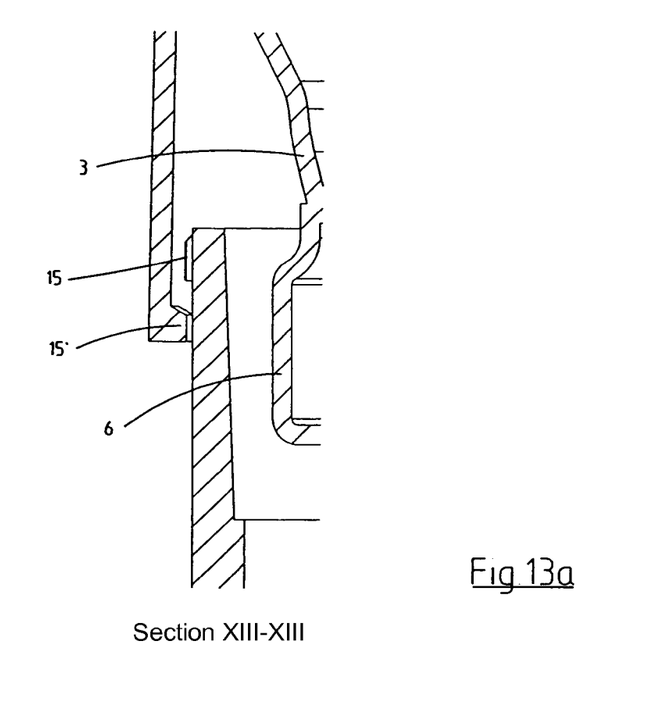
FIG. 13a: a section along the line F-F from FIG. 13.

FIG. 12*a* shows an enlarged detail (section along the line E-E from FIG. 12) of the bayonet lock. It can be clearly seen here that, in the operating position, projections 15, 15' of the bayonet lock make it impossible for the second housing part 2 to be removed from the first housing part 1. By the same token, the first and second housing parts 1, 2 are configured in such a way that they can be moved towards each other in order to actuate the valve 5. FIG. 13*a* shows how, in the release position, when the first and second housing parts 1, 2 have been rotated with respect to each other as depicted, the projections 15, 15' of the bayonet lock are not engaged and thus allow the second housing part 2 to be removed.

The device shown in the figures has an electronic unit 16 to record the administered doses of the sprayable substance. This unit comprises a switch 17 that is actuated when the first and second housing parts are moved towards each other in order to actuate the valve 5.

As shown in FIGS. 4 to 9, the electronic unit 16 is accommodated in a holder that is formed in the first housing part 1 and that, in the embodiment shown, consists of a chamber 18 having an essentially slit-like shape. The chamber 18 protects the electronic unit 16 against damage and manipulation.

The electronic unit 16 has a board 19 that is configured as a printed circuit board to accommodate and electrically connect the requisite components with each other. The switch 17 is likewise arranged on the board 19 and has an electric contact that is opened and closed when the switch is actuated. In the embodiment shown, the board 19 is held securely in the chamber 18 by latching members 21 (see FIG. 9). The assembly is simple because the board 19 can be prefabricated and thus merely needs to be inserted into the chamber 18. As an alternative, the board 19 can also be cast into the chamber 18.

Figures 5, 5A:
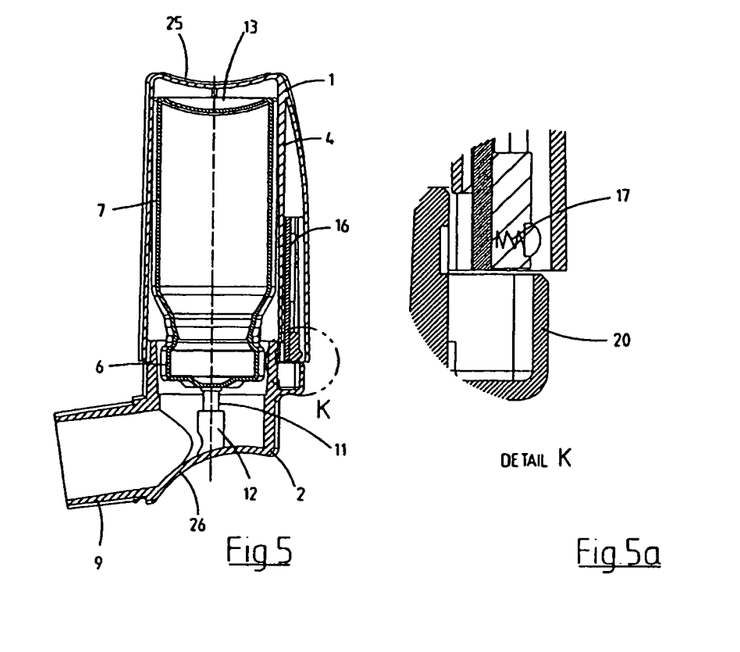
FIG. 5: a section through the device from FIG. 1 along the switch in the non-actuated position.
FIG. 5a: an enlarged depiction of the detail K from FIG. 5.
Figure 6:
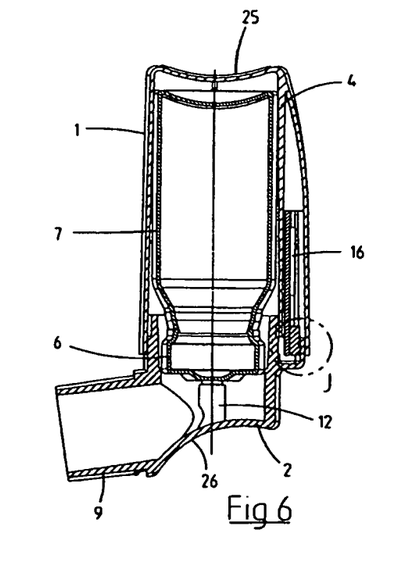
FIG. 6: a section through the device from FIG. 1 along the switch in the actuated position.
Figure 6A:
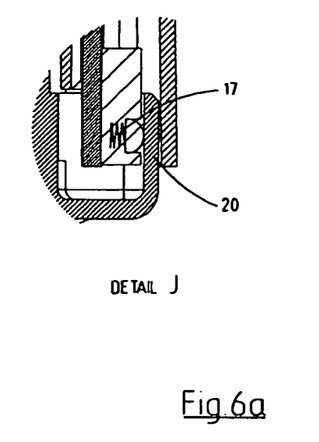
FIG. 6a: an enlarged depiction of the detail J from FIG. 6.

The switch 17 schematically shown in FIGS. 5 to 6*a* is actuated by an actuating section 20 that is arranged on the second housing part 2. Here, too, it can be seen that the switch 17 is arranged on the end section of the first housing part 1 facing the second housing part 2. Here, the switch 17 is not situated on the canister 3, but rather, the switch 17 is arranged in the chamber 18 of the first housing part in such a way that the switch 17 is protected and cannot be inadvertently actuated. Improper triggering of the switch 17 is also made more difficult since the switch 17 cannot be reached with a finger. The projecting actuating section 20 is arranged on the second housing part 2 in such a manner that it extends into the chamber 18 when the first and second housing parts 1, 2 move towards each other in order to actuate the valve 5. This position is depicted in FIGS. 6 and 6*a* while FIGS. 5, 5*a* show the non-actuated position.

The electronic unit 16 in the embodiment shown records the number of administered doses or the number of actuations of the valve 5. Towards this end, the board 19 of the electronic unit 16 has a computing unit, a data storage unit and a source of energy in the form of a battery (not shown in detail) so that the administered doses recorded by the switch 17 during which an electric contact is closed can each be counted. If the maximum number of actuations of the valve 5 (corresponding to the specific holding capacity of the canister 3) in the electronic unit 16 has been stored in advance, the amount of substance left or the remaining number of possible doses of the sprayable substance can be directly ascertained. The specific maximum number of actuations can be entered by storing the applicable values within the scope of a programming operation or else by means of a coding switch or the like.

Figure 7:
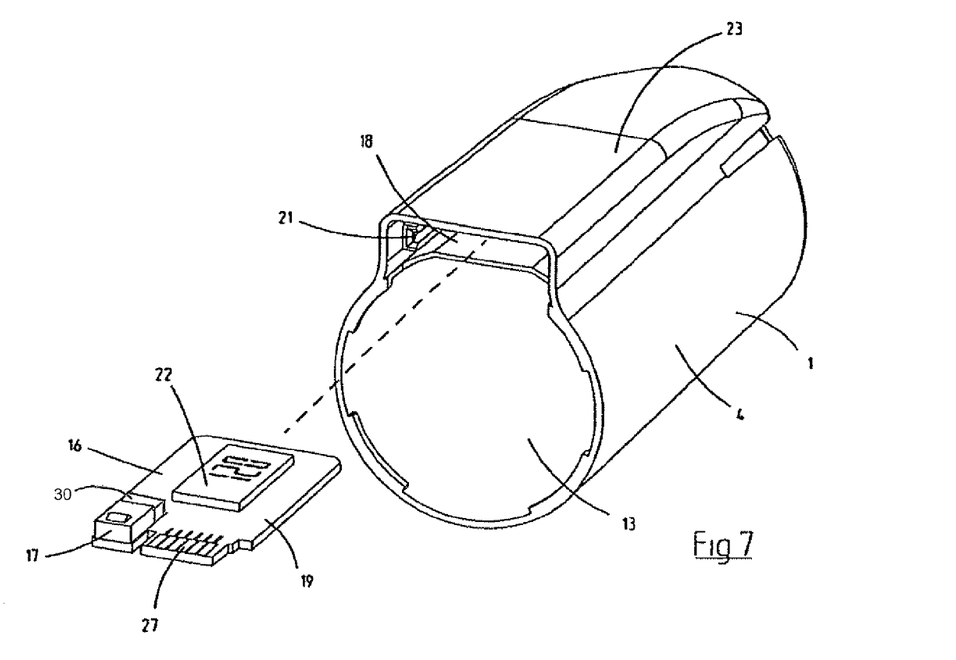
FIG. 7: a perspective view of the first housing part and of the electronic unit to record the administered doses of the sprayable substance, as shown in the device from FIG. 1, prior to being assembled.
Figure 8:
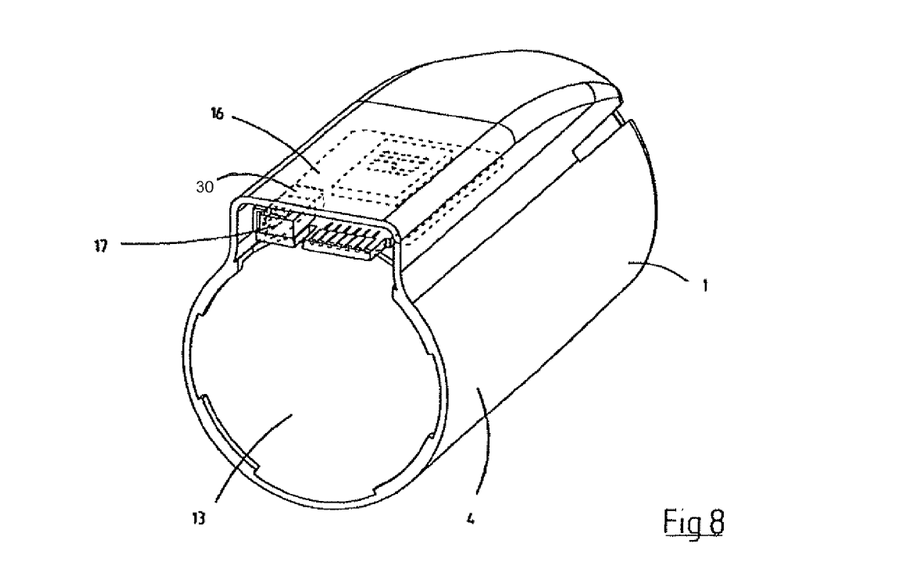
FIG. 8: a perspective view of the first housing part and of the electronic unit to record the administered doses of the sprayable substance, as shown in the device from FIG. 1, after being assembled.
Figure 9:
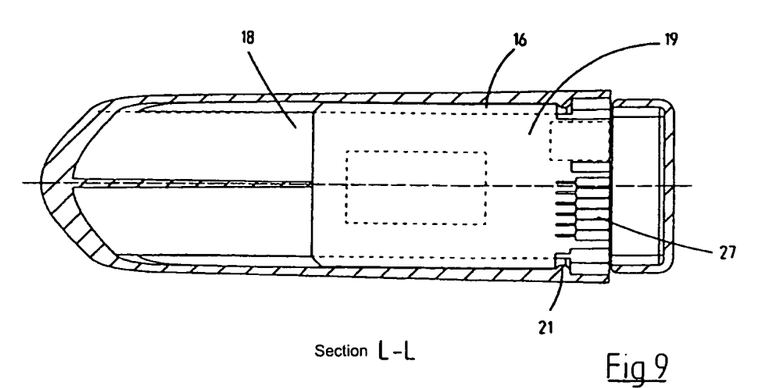
FIG. 9: a partial sectional view of the first housing part from FIG. 8 with the electronic unit to record the administered doses of the sprayable substance.

The acquired information is shown on a small visual display 22 that is configured as an LCD and that can be seen from the outside. Accordingly, the cover 23 of the chamber 18 is made of a transparent material, especially plastic. As an alternative or in addition to the visual display, as shown in FIGS. 7 and 8, an acoustic signal transmitter 30 can be provided.

More complex functions are possible if the electronic unit 16 has a clock. In such a case, the user can, for example, be visually and/or acoustically reminded when it is time for the next inhalation of the medication. Furthermore, the expiration date can be displayed to the user or else a warning to this effect can be given. It is also practical to give a warning as soon the remaining quantity of the sprayable substance falls below a certain level. Moreover, the specific points in time for the inhalation or the applicable doses or the number of doses that have been administered can all be stored.

It is likewise possible to configure the electronic unit 16 in such a way that the stored information can be read out via an interface. In this case, for example, it can be checked when and in what dose the drug in question has been taken. For this purpose, the unit 16 is provided with contacts 27. Alternatively, wireless data transmission can be provided.

If the valve 5 is configured as a metering valve, it is not necessary to record the duration of the actuation of the valve 5 since each actuation delivers the a uniform amount of the sprayable substance. However, if a simple valve is employed, the device can also be configured in such a way that it records the duration of the administration of the sprayable substance and in this case, the amount administered can also be ascertained.

The first and second housing parts 1, 2 are injection-molded parts made of plastic. Here, the first housing part 1 is made of transparent plastic so that not only the display 22 but also the information printed on the canister 3 is visible.

The presented device has only a small number of components and can be manufactured cost-effectively. Consequently, it also lends itself for disposable use. In this context, the term disposable use applies when the device is replaced together with the matching canister. Naturally, multiple use is likewise feasible. In this case, a reset switch, for instance, has to ensure that the electronic unit 16 is set to its original state when the canister is replaced.

The invention claimed is:

1. A device for dosed administration of a sprayable substance comprising:
   an electronic unit to record the administered doses;
   a first housing part forming a receptacle for a canister having a valve and containing the sprayable substance;
   a second housing part movable relative to the first housing part and having an actuation section for acting upon the valve to cause the valve to deliver the sprayable substance,
   the electronic unit having a switch actuated by the relative movement of the first housing part and the second housing part,
   the first and second housing parts being movable between a first rotational position and a second, different rotational position relative to each other, wherein said first rotational position is an operating position in which the first and second housing parts are movable in an axial direction with respect to each other to actuate the valve and deliver the sprayable substance, said second housing part not being removable from said first housing part in said first rotational position, and
   wherein said second rotational position is a release position in which the second housing part is removable from the first housing part in said second rotational position and are not removable from each other in another rotational position spaced from said second rotational position, and the first and second housing parts are incapable of being moved axially with respect to each other in such a way that the valve could be actuated by the second housing part.

2. The device according to claim 1 wherein the first and second housing parts are joined via a bayonet lock.

3. The device according to claim 1 wherein the first and second housing parts have stops that only allow an axial movement of the first and second housing parts towards each other when in the operating position.

4. The device according to claim 1 wherein the switch is at least one of a mechanical switch, a proximity switch, an electromagnetic switch and an optical switch.

5. The device according to claim 1 wherein the switch is configured to not be situated on the canister.

6. The device according to claim 1 wherein the canister has a canister body and a canister head with the valve for the dosed administration of the sprayable substance, the canister capable of being accommodated in the receptacle.

7. The device according to claim 6 wherein the first housing part has a hollow shaft, the canister body capable of being partially or completely accommodated in the hollow shaft.

8. The device according to claim 6 wherein the second housing part has a first section to accommodate the canister head and a hollow second section.

9. The device according to claim 8 wherein the hollow second section is configured as a mouthpiece and/or nosepiece.

10. The device according to claim 1 wherein the electronic unit records at least one of a number and a duration of the administered doses.

11. The device according to claim 1 wherein the electronic unit has an electronic computing unit and an electronic data storage unit, the administered doses recorded by the switch being countable in the electronic data storage unit.

12. The device according to claim 1 wherein the electronic unit has a visual display capable of showing information about a number of administered doses and/or a number of doses remaining.

13. The device according to claim 1 wherein the electronic unit to record has an acoustic signal transmitter.

14. The device according to claim 1 wherein the electronic unit having the switch to record the administered doses is arranged on or in one of the first and second housing parts and the switch is actuated by an actuation element provided on the other of the first and second housing parts when the first and second housing parts move with respect to each other.

15. The device according to claim 1 wherein the device is configured as an inhaler.

16. The device according to claim 1 further comprising the canister, the canister being filled at least partially with the sprayable substance and being accommodated in the receptacle.

17. The device according to claim 1 wherein the sprayable substance is a drug.

18. The device according to claim 1 wherein the sprayable substance is kept under excess pressure in the canister.

19. The device according to claim 1 wherein the valve of the canister is configured as a metering valve that delivers a uniform amount of the sprayable substance every time it is actuated.

20. A device for dosed administration of a sprayable substance comprising:
   an electronic unit to record the administered doses;
   a first housing part forming a receptacle for a canister having a valve and containing the sprayable substance;
   a first stop attached to the first housing part and defining a chamber;
   a second housing part movable relative to the first housing part and having an actuation section for acting upon the valve to cause the valve to deliver the sprayable substance;
   a second stop attached to the second housing part and configured to project into and matingly engage the chamber when the first stop and the second stop are aligned with each other;
   the electronic unit having a switch actuated by the relative movement of the first housing part and the second housing part, the first and second housing parts being movable between a first rotational position and a second rotational position, said first and second rotational positions being single positions and different positions, wherein in the first rotational position, the first stop and the second stop are aligned with each other such that the second stop engages the chamber of the first stop enabling the second housing part to move in an axial direction relative to the first housing part to actuate the valve and deliver the sprayable substance, and wherein in the second rotational position, the first stop and the second stop are not aligned with each other such that the second housing part is removable from the first housing part in said second rotational position and are not removable from each other in another rotational position spaced from said second rotational position, and the first and second housing parts are incapable of being moved axially with respect to each other in such a way that the valve could be actuated by the second housing part.

\* \* \* \* \*

UNITED STATES PATENT AND TRADEMARK OFFICE
CERTIFICATE OF CORRECTION

PATENT NO. : 9,004,062 B2  
APPLICATION NO. : 12/319656  
DATED : April 14, 2015  
INVENTOR(S) : Lang et al.

Page 1 of 1

It is certified that error appears in the above-identified patent and that said Letters Patent is hereby corrected as shown below:

Title Page below Item (22) insert

--(30) Foreign Application Priority Data

July 11, 2006  (DE) . . . . . . . . . . . . 10 2006 032 293.2

July 9, 2007 . . . . . . . . . . . . . . . . . PCT/EP2007/006052--.

Signed and Sealed this
Twenty-ninth Day of September, 2015

Michelle K. Lee
*Director of the United States Patent and Trademark Office*